US 6,572,565 B2

(12) United States Patent  
Daley et al.

(10) Patent No.: US 6,572,565 B2
(45) Date of Patent: Jun. 3, 2003

(54) BLOOD SAMPLING ASSEMBLY WITH A RETRACTABLE NEEDLE

(75) Inventors: Stuart Daley, Camarillo, CA (US); Earl Boyer, Siml Valley, CA (US); Thomas Coughlin, Tulsa, OK (US); Martin E. Smith, Camarillo, CA (US)

(73) Assignee: Maxxon, Inc., Tulsa, OK (US)

( * ) Notice: Subject to any disclaimer, the term of this patent is extended or adjusted under 35 U.S.C. 154(b) by 0 days.

(21) Appl. No.: 09/974,920

(22) Filed: Oct. 10, 2001

(65) Prior Publication Data

US 2003/0069518 A1 Apr. 10, 2003

(51) Int. Cl.[7] .............................. A61B 5/00; A61M 5/00
(52) U.S. Cl. ...................... 600/573; 600/576; 604/110; 604/198
(58) Field of Search .................. 600/573, 575–579, 600/583; 604/110, 187, 192, 195, 197, 198, 220, 225, 226, 263

(56) References Cited

U.S. PATENT DOCUMENTS 5,423,758 A * 6/1995 Shaw .......................... 604/110
5,562,103 A * 10/1996 Sak ............................ 600/576
6,063,040 A * 5/2000 Owen et al. ................. 600/573
6,077,245 A * 6/2000 Heinrich et al. ............. 604/110
6,186,960 B1 * 2/2001 Tripp et al. .................. 600/576
6,280,401 B1 * 8/2001 Mahurkar .................... 600/576
6,471,677 B2 * 10/2002 Domici, Jr. .................. 604/198

* cited by examiner

*Primary Examiner*—Charles A. Marmor, II
(74) *Attorney, Agent, or Firm*—Loren G. Helmreich; Browning Bushman, P.C.

(57) ABSTRACT

The blood sampling assembly includes a retractable double-ended needle so that a vial may be passed through an opposed end of the needle to obtain a blood sample. The assembly includes a hollow cylinder including circumferentially spaced seat tabs which allow a needle seat and the needle supported thereon to be released upon rotation of tube with respect to hollow cylinder. The extractor assembly includes a stopper for maintaining a vacuum within tube to withdraw the needle to a retracted position within the tube upon rotation of the tube, the end cap, and the stopper retainer. A stopper tab positioner rotationally connects the stopper to the cylinder.

20 Claims, 6 Drawing Sheets

BLOOD SAMPLING ASSEMBLY WITH A RETRACTABLE NEEDLE

FIELD OF THE INVENTION

The present invention relates to devices for obtaining blood samples from a patient, typically for diagnostic testing. More particularly, the invention relates a blood sampling assembly with a retractable needle to protect the health care worker from being inadvertently pricked by the needle after the blood withdrawal operation.

BACKGROUND OF THE INVENTION

Various types of syringes have been devised over the past twenty years, including syringes intended to minimize or prevent the likelihood of the syringe needle pricking the operator during use. U.S. Pat. Nos. 4,790,827, 5,415,648, 6,193,695 and Re 33558 disclose various configurations for a safety syringe. In the '695 Patent, a piston assembly is movable within the syringe body to create a vacuum which is used to withdraw the needle into the syringe. U.S. Pat. No. 6,126,618 discloses a complex device for obtaining blood from a patient, and is particularly designed to collect whole blood from a healthy donor.

Unique conditions are presented when devising a device for taking one or more blood samples while simultaneously protecting the health care worker from infection due to accidental contact with a contaminated needle. Blood samples are commonly obtained using a sterile device which is disposed after a single use. The blood sampling device ideally is simple to operate, is relatively economical to manufacture, is easy to use, and is highly reliable in its operation. In order to prevent the likelihood of infecting the health care worker by a needle prick, the needle may be withdrawn into the device so that the needle is protected from contacting the health care worker.

Conventional hypodermic syringes are less than desirable if blood is to be withdrawn from a patient for conducting diagnostic tests. The most widely used blood sampling devices use a cylinder with a double ended needle, which may be provided with a protective cap over one or both ends of the needle prior to use by the health care worker. The needle hub is conventionally threaded to the cylinder to locate the posterior needle end within the cylinder. The anterior end of the needle extending from the cylinder is inserted into the patient, and one or more evacuated tubes or vials are then positioned partially within the cylinder so that the opposing posterior end of the needle pierces through a stopper or membrane in the vial, thereby withdrawing blood into the vial. When the sample tube has been filled to its desired extent, the vial is withdrawn from the cylinder and, if desired, another vial is inserted into the cylinder to obtain another blood sample. By removing filled tubes and inserting new evacuated tubes, multiple samples can be taken without removing the anterior end of the needle from the patient. Double-ended needles are readily available from commercial sources. U.S. Pat. No. 6,017,317 discloses one type of assembly suitable for collecting various samples of blood in vacuum tubes.

Hospital and clinical practice requires that blood specimens be taken simply, quickly, and with inexpensive and readily disposable equipment. Many prior art blood sampling devices are intended to perform the function of minimizing the likelihood of an inadvertent needle stick, but the devices suffer from numerous drawbacks. Some devices require complex operations which render the devices unacceptable to many health care workers. Other devices themselves are relatively complex, thereby making the devices expensive to manufacture, particularly since the devices are preferably not reusable. Other devices require significant changes or modifications to conventional medical procedures, thereby requiring expensive and time consuming training.

U.S. Pat. Nos. 5,219,333 and 6,152,901 disclose blood collection devices which require that the operator move a slide along a cylinder to withdraw the needle into the cylinder. U.S. Pat. No. 4,643,199 discloses a blood sampling device which utilizes a combination of twisting and axial movements to secure a needle within the cylinder. U.S. Pat. No. 5,201,716 discloses a blood sampling device with a mechanism intended to eject the needle assembly from the cylinder. Other blood sampling devices with retractable needles are disclosed in U.S. Pat. No. 4,850,374 and 5,086,780. A blood collection device with a needle mounted eccentric relative to the cylinder is disclosed in U.S. Pat. No. 5,938,622.

U.S. Pat. No. 6,186,960 discloses a blood collection device which withdraws the needle into a vacuum tube after use. The device requires the health care worker to apply an axial force to break a mechanical connection between the cylinder and a needle seat. Accordingly the device is considered difficult to operate since the force required to break the mechanical connection is both significant and variable.

Accidental needle pricks typically result in the need for numerous blood tests for diseases such as HIV and hepatitis. Significant costs are incurred to test health care workers involved in taking blood samples, and unfortunately many health care workers have become infected with diseases transmitted when the blood sampling needle inadvertently pricks the health care worker.

The disadvantages of the prior art are overcome by the present invention, and an improved blood collection device is hereinafter disclosed which may be easily and reliably used by health care personnel. The device advantageously provides for the withdrawal of the needle into a vacuum tube by the mere rotation of the tube relative to the cylinder.

SUMMARY OF THE INVENTION

In an exemplary embodiment, the blood sampling assembly includes a double ended needle supported on a cylinder. The anterior end of the needle is intended for inserting into the patient, and the opposing posterior end of the needle is intended to perforate a stopper or membrane of an evacuated tube or vial placed in the cylinder.

In a preferred embodiment, the hollow cylinder has a needle end and an opposing extractor end. The evacuated tube or vial is thus inserted into the extractor end to perforate the stopper and fill the vial with blood. The cylinder includes circumferentially spaced needle seat tabs and needle seat slots each between spaced needle seat tabs. A needle seat is provided for supporting the needle on the cylinder, and includes circumferentially spaced cylinder tabs each in engagement with a respective needle seat tab to temporarily fix the needle seat to the cylinder. The needle seat also includes cylinder slots each between spaced cylinder tabs and circumferentially aligned with a respective needle seat tab to release the needle seat and the needle from the cylinder, as discussed subsequently.

An extractor assembly for positioning at least partially within the extractor end of the cylinder includes a closed end tube containing a vacuum, and a stopper in sealed engagement with an interior surface of the tube and axially movable between an initial position and a needle retracted position. When the tube is inserted into the cylinder, the stopper receives therein the posterior end of the needle. A stopper tab is axially secured to the stopper and engages the stopper tab stop on the cylinder to prevent rotation of the stopper tab when the tube is rotated. A stopper retainer is rotatable with the tube between a retaining position for temporarily fixing the stopper in the initial position and a release position for releasing the stopper to move to the needle retracted position. The stopper retainer includes a retainer tab in engagement with the stopper tab when the stopper retainer is in the retaining position and a slot in circumferential alignment with the stopper tab when the stopper retainer is in the release position. The extractor assembly further includes an end cap rotatable with the tube and a needle seat stop for engagement with the cap stop. Rotation of the tube rotates the end cap, the stopper retainer and the needle seat relative to the cylinder to release the needle seat and the stopper, so that the needle moves with the stopper to the needle retracted position by the vacuum within the tube.

In a preferred embodiment, the stopper retainer includes a cap stop and the cap includes a retainer stop, such that engagement of these stops prevents rotation of the stopper relative to the cap. The annular stopper retainer includes a throughbore for passing the needle seat through the stopper retainer when the stopper is moved to the needle retracted position. A similar throughbore is provided in the annular end cap. A stopper tab positioner engages both the stopper tab stop and the stopper tab to prevent rotation of the stopper tab during rotation of the tube.

According to the method of the invention, circumferentially spaced cylinder tabs on the needle seat each engage a respective needle seat tab to support the needle seat on the cylinder. The extractor assembly is inserted at least partially within the extractor end of the cylinder such that the opposed end of the needle is within or passes through the stopper. The health care worker then rotates the tube, which rotates the end cap and the stopper retainer from a retaining position to a release position, thereby releasing the needle seat from the cylinder and simultaneously releasing the stopper from the stopper retainer. The needle, the needle seat and the stopper move together as an assembly into the tube when the stopper moves to the needle retracted position by the vacuum within the tube.

It is an object of the present invention to provide an improved blood sampling assembly for retracting a needle and needle seat from a cylinder and thereby shielding the needle after completion of a blood collection procedure. It is a related object of the invention to provide a relatively inexpensive blood sampling assembly which significantly reduces the likelihood of the health care worker becoming pricked with the needle.

A related object of the invention is to provide a blood sampling assembly which utilizes a vacuum tube for withdrawing the needle into the vacuum tube upon rotation of the tube relative to the cylinder.

It is a feature of the present invention that the blood sampling assembly may be easily and reliably used to take various blood samples using a conventional evacuated vial, and thereafter the needle may be withdrawn into a vacuum tube for disposal.

Another feature of the invention is that the stopper may be positioned closely adjacent the end of the tube, so that substantially the full length of vacuum in the tube is available to retract the needle into the tube.

A significant advantage of the present invention is that the blood sampling assembly is relatively inexpensive, and uses techniques substantially similar to conventional techniques for obtaining blood samples.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
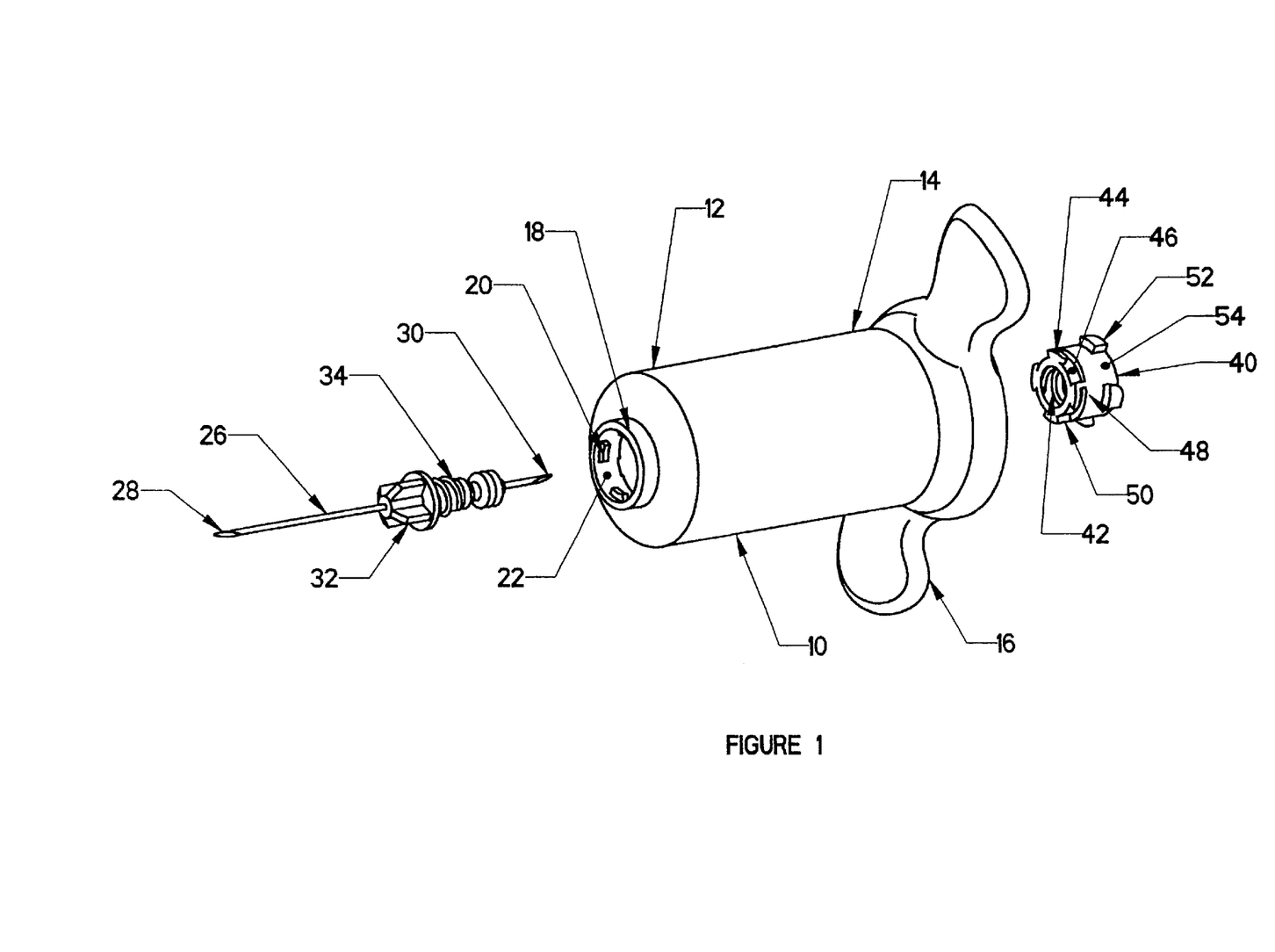
FIG. 1 is an exploded view of a needle, cylinder, and cylinder seat according to the present invention.
Figure 6:
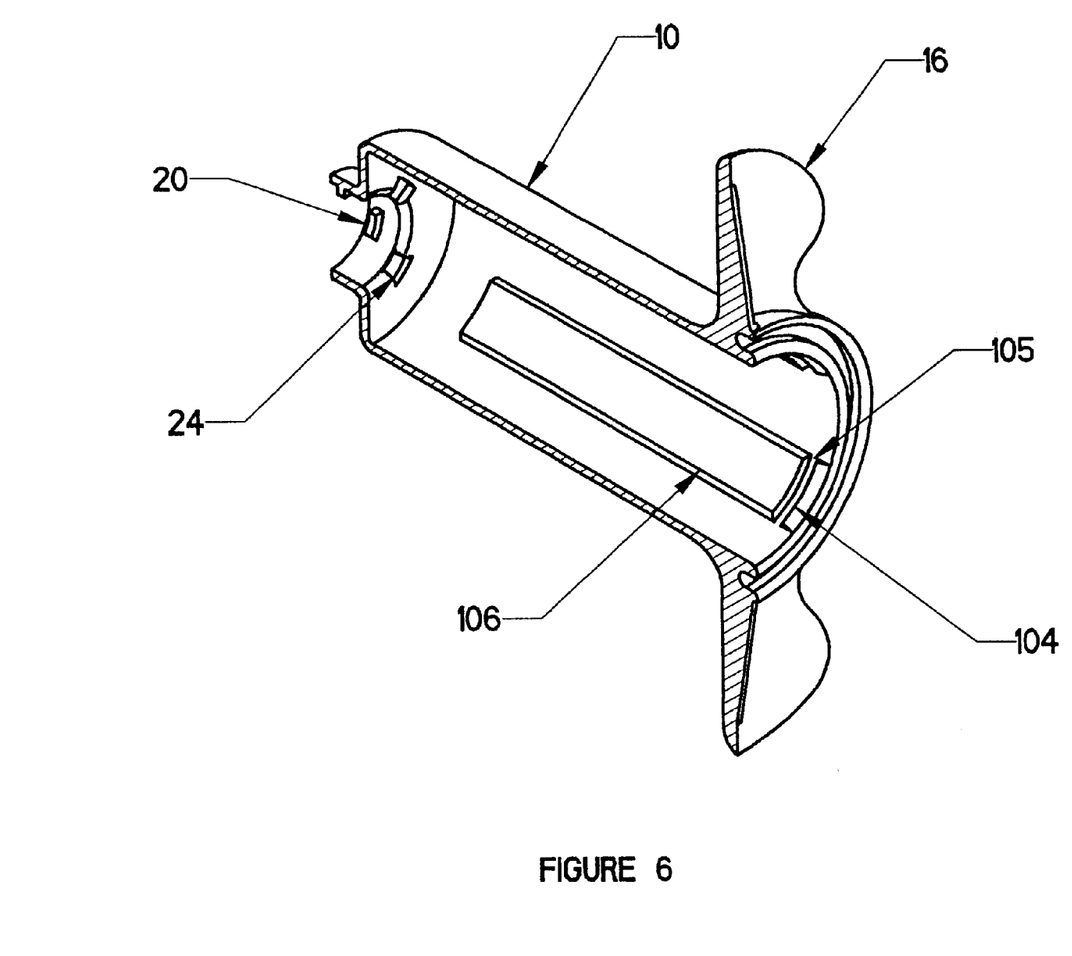
FIG. 6 is a cross-sectional view of the hollow cylinder, showing the stopper tab stops.

FIG. 1 depicts one embodiment of a cylinder 10 according to the present invention. The hollow cylinder 10 includes a needle end 12 and an opposed extractor end 14. The extractor end is preferably provided with a pair of radially opposing finger tabs 16 which allow the health care worker to position the cylinder with one hand when a vial is inserted with the other hand to obtain a blood sample. FIG. 1 depicts that the cylinder 10 further includes a reduced diameter sleeve portion 18 which includes a plurality of circumferentially spaced needle seat tabs 20. Preferably two or more needle seat tabs are uniformly positioned about the circumference of the cylinder, and a preferred embodiment includes four tabs 20 spaced at 90° intervals. The spacing between the needle seat tabs 20 defines needle seat slots 22 each between two spaced needle seat tabs. The cylinder 10 also includes a plurality of stopper tab positioner stops with positioner slots 24 between the stops, as shown in FIG. 6. Cylinder 10 also includes cap guides 106 and tube locks 104 discussed subsequently.

The blood sampling assembly of the present invention may use a conventional double ended needle 26. The anterior end 28 of the needle is intended for inserting into the patient, while the posterior end 30 will be positioned within the cylinder 10. The needle 26 includes a conventional plastic hub 32, which includes a spiral thread 34 for securing the needle 26 to the needle seat. Although not shown in FIG. 1, the needle may be provided with a protective plastic sheath which covers the anterior end 28 of the needle. Optionally another sheath may be provided for covering the posterior end 30 of the needle. An optional elastomeric cushioning member may be provided on the needle for engagement with the end of a vial when taking a blood sample.

The needle seat 40 includes an interior thread 42 for engagement with the thread 34 on the needle 26. Seat 40 also includes circumferentially spaced tabs or cylinder protusions 44 and cylinder slots 46 between spaced cylinder protusions. Each cylinder protusion 44 is intended for engagement with a respective needle seat tab 20 to temporarily fix the needle seat 40 and thus the needle to the cylinder 10. The slots 46 are positioned such that, when circumferentially aligned with the needle seat tabs 20, the seat 40 will be released from the needle seat tabs 20 on the cylinder 10. The four arcuate shaped grooves 48 are thus each sized to receive a respective tab 20 so that, when the needle seat is rotated relative to the cylinder, each of the needle seat tabs 20 will be positioned in a respective groove and rearward of a respective protusion 44. Each of the grooves 48 further includes a stop needle seat tab surface 50 which engages an edge of a respective needle seat tab 20 when the needle seat has been rotated to the release position. FIG. 1 also depicts four circumferentially spaced cap stops 52 thereon, with cap slots 54 being spaced between the cap stops. The purpose of the cap stops 52 will be explained further below. For the present, it should be understood that the needle seat 40 may be inserted into the extractor end of the cylinder 10 and fitted in place with the slots 46 aligned with the needle seat tabs 20. The needle seat may then be rotated in the clockwise direction (when viewed from the front) as shown in FIG. 1 to secure the position of the needle seat on the cylinder. The needle 26 may then be threaded to the needle seat, so that the needle will be reliably positioned relative to the needle, with the posterior end 30 of the needle positioned within the cylinder 10.

The interior of the cylinder 10 preferably includes a bore sized for receiving a conventional evacuated vial (not shown). Circumferentially spaced guide rails 106 guide both the extractor assembly 60 and a vial when inserted into the cylindrical 10. The vial is inserted into the extractor end of the cylinder 10 so that the posterior end 30 of the needle 26 pierces through a stopper or membrane in the vial, thereby withdrawing blood into the vial. When the vial has been filled to its desired extent, the vial is withdrawn from the cylinder. If desired, another vial is inserted into the cylinder to obtain another blood sample. Guide rails 106 on cylinder 10 and guide slot 107 on cap 82 provide easy alignment when inserting the extractor assembly into the cylinder.

Figure 2:
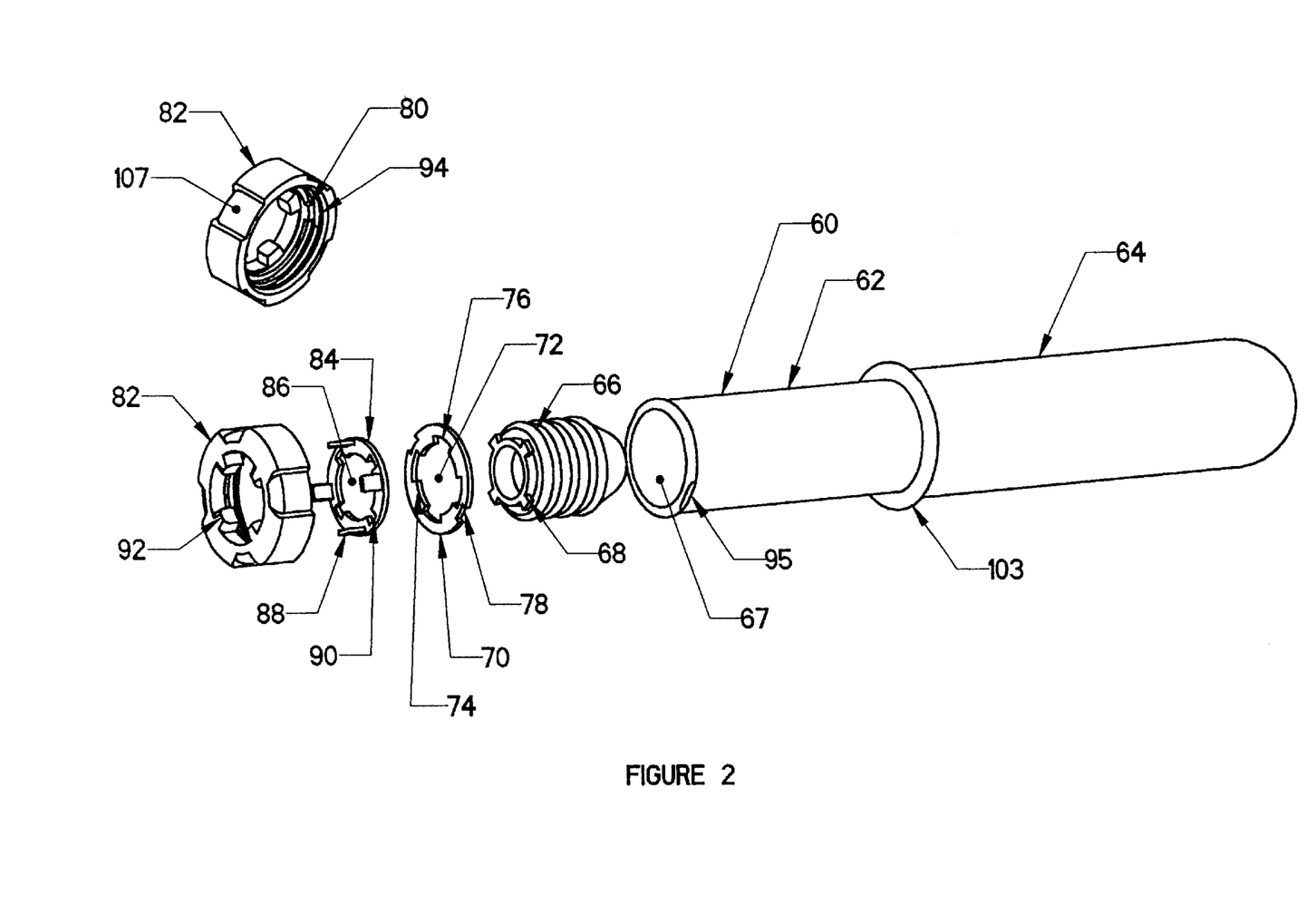
FIG. 2 is an exploded view of the components of the needle extractor assembly, including a vacuum tube, stopper, stopper retainer, stopper tab positioner, and end cap.

FIG. 2 discloses the components of an extractor assembly 60 which is positioned at least partially within the extractor end of the cylinder 10 for withdrawing the needle into the extractor assembly. The assembly 60 includes a closed end tube 62 which preferably includes a rubber, plastic or elastomeric material sheath 64 for facilitating rotation of the tube relative to the cylinder 10 and locking the tube 62 to the cylinder 10. A stopper 66 is provided for sealed engagement with the interior surface 67 of the tube, and is positioned closely adjacent the open end of the tube so that substantially the entire length of the tube 62 contains a vacuum. As discussed subsequently, the stopper 66 is axially movable between an initial position as shown in FIG. 4 to a needle retracted position, as shown in FIG. 5, thereby withdrawing the needle into the interior of the cylinder 10 and the tube 62.

At least one stopper tab 68 is axially secured to the stopper 66 and, in a preferred embodiment, four circumferentially spaced stopper tabs 68 are axially and rotationally secured to the stopper 66. As discussed subsequently, each of the stopper tabs 68 are designed for engagement with a stopper tab positioner stop 24 on the cylinder 10 to prevent rotation of the stopper tab 68 and thus the stopper 66 with the tube 62. Preferably this engagement is accomplished with the stopper positioner 84 therebetween, as discussed below. An annular stopper retainer 70 includes a throughbore 72, and is rotatable with the tube between a retaining position for temporarily fixing the stopper 66 in the initial position as shown in FIG. 4 and a release position for releasing the stopper to move to the needle retracted position as shown in FIG. 5. The stopper retainer 70 includes four circumferentially spaced retainer tabs 74 which engage the rearward side of the four stopper tabs 68 when the stopper is in the retaining position. Four circumferentially spaced slots 76 are in alignment with the four stopper tabs 68 when the stopper retainer is in the release position. The stopper retainer 70 further includes two radial opposing slots 78 defining cap stops designed for engaging similarly positioned retainer stops 80 on the end cap 82, thereby rotationally locking the stopper retainer 70 to the end cap 82.

FIG. 2 also discloses an annular stopper positioner 84 which includes a throughbore 86. The stopper positioner includes four axially extending tabs 88 each designed for engagement with a stopper positioner stop 24 on the cylinder 10 (see FIG. 6), thereby preventing rotation of the stopper positioner 84 with respect to the cylinder 10. The stopper positioner 84 also includes four circumferentially spaced slots 90 each sized to receive one of the four tabs 68 on the stopper 66, thereby rotationally locking the stopper positioner 84 to the stopper tabs 68. Finally, the end cap 82 includes four circumferentially spaced needle seat stops 92 for engagement with the cap stops 52 on the needle seat 40. The cap 82 includes cap plates 94 which are sized to fit within the cut outs 95 in the end of the tube 62. Accordingly, the tube 62 is rotationally connected to the cap 82 by the cap plates 94 and the tube cut outs 95, and the cap 82 is rotationally connected to both the needle seat 40 by the needle seat stops slots 92 and the stopper retainer 70. Rotation of the tube 62 relative to the cylinder 10 thus rotates the end cap 82, the needle seat 40 and the needle 26, and the stopper retainer 70 to release both the needle seat and the stopper to allow the stopper to be moved to the needle retracted position by the vacuum within the tube.

Figure 4:
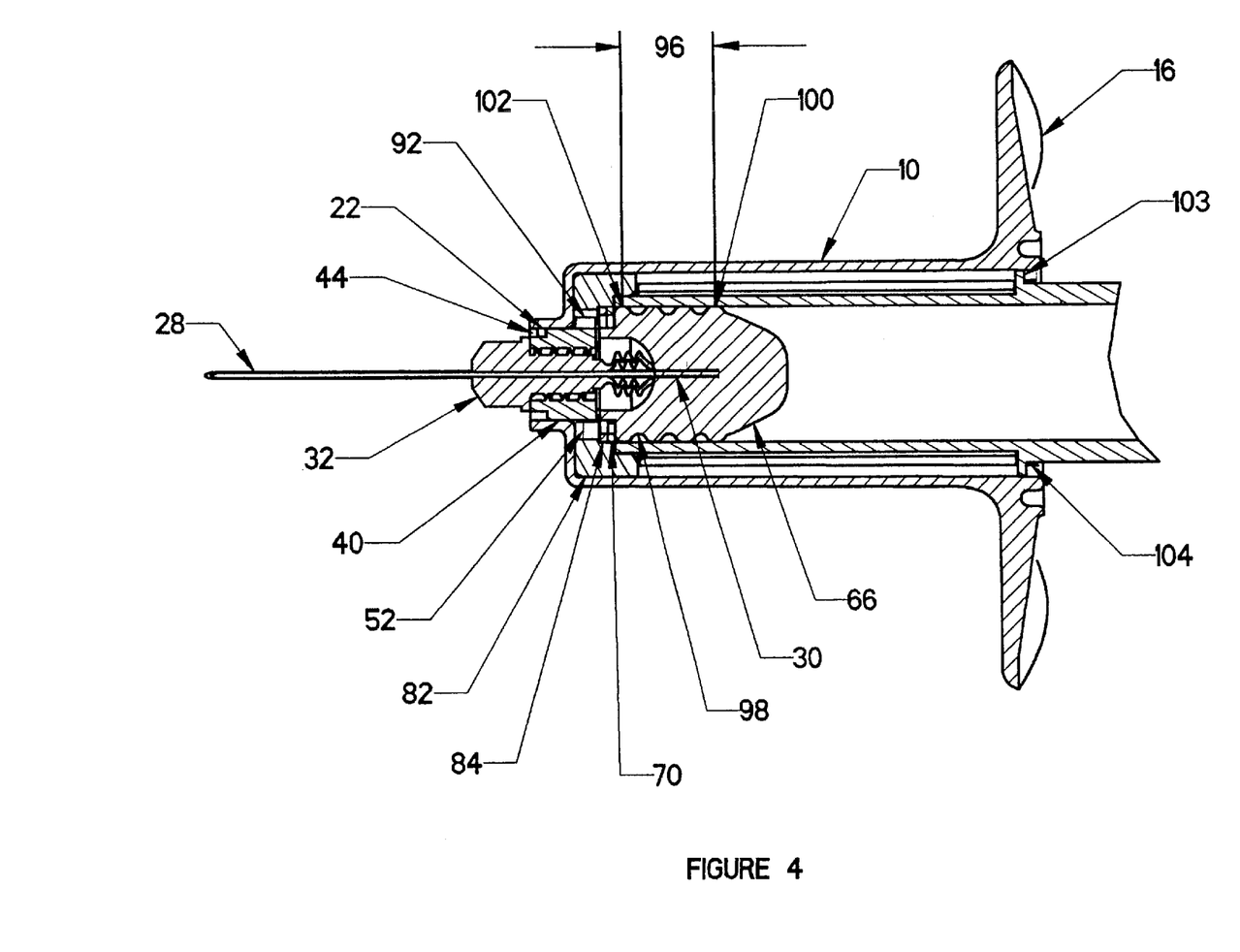
FIG. 4 is a cross-sectional view of a portion of the assembly when the vacuum tube has been inserted into the cylinder so that the needle penetrates the stopper.
Figure 5:
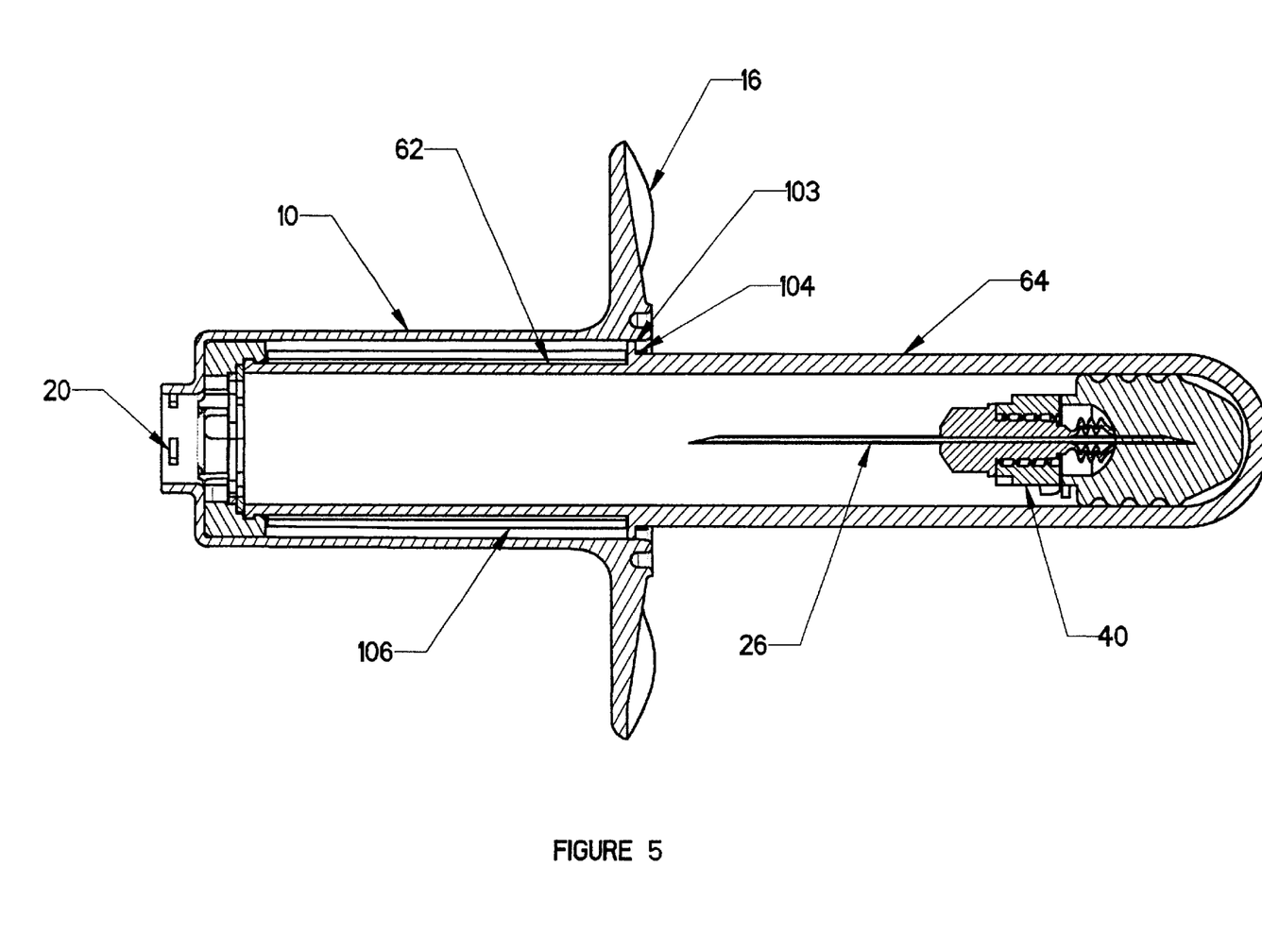
FIG. 5 is a cross-sectional view of a blood sampling assembly according to the present invention with the stopper moved to the needle retracted position.

Referring briefly to FIG. 4, a stopper 66 is shown in its initial position within the tube 62. Since the stopper 66 maintains vacuum within the closed end tube 62 for a substantial period of time, the stopper 66 has relatively long sealing length 96 to reliably maintain vacuum within the tube. This axial sealing length may be interrupted to further enhance sealing reliability by various techniques, including providing axially spaced grooves 98 at selected spacings along the axial sealing length 96. The term "axial sealing length" when referring to the stopper 66 means the axial length between the initial sealing surface 100 on the stopper and the final sealing surface 102 on the stopper. One of the features of the present invention is that the stopper 66 is positioned within the tube 62 such that substantially the full length of the vacuum tube is available for withdrawing the stopper to the needle retracted position. This desired relationship is maximized in the FIG. 4 embodiment, and preferably the final sealing surface 102 is within one axial length of the stopper sealing length 96 from the open end of the tube 62.

Figure 3:
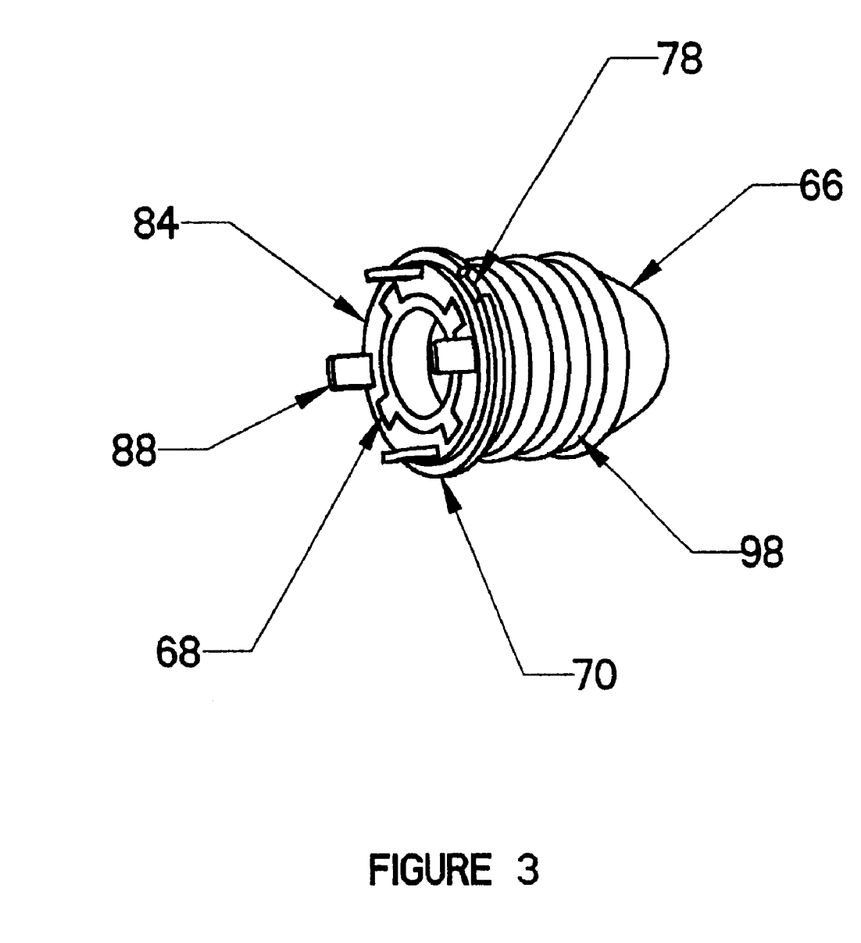
FIG. 3 is a pictorial view of a stopper with the stopper retainer and the stopper tab positioner rotatably securing the stopper to the stopper tab positioner.

FIG. 3 illustrates the stopper 66 with the annular stopper retainer 70 positioned over the stopper tabs 68. Tabs 68 are thus received within slots 76, and the stopper retainer 70 rotated to axially lock the tabs 74 behind the tabs 68. The stopper positioner 84 may then be pressed against the stopper retainer 70, with the slots 90 aligned for receiving the tabs 68, thereby rotatably securing the stopper positioner 84 to the stopper tabs 68 and thus the stopper 66. FIG. 3 also depicts the slot 78 in the stopper retainer 70 which acts as a stop against the retainer stop 80 on the end cap 82, thereby rotationally connecting the stopper retainer 70 to the end cap 82.

FIG. 3 shows the axially extending tabs 88 on the stopper positioner 84, which rotationally connect or lock the stopper positioner 84 to the cylinder 10 by engagement with stopper positioner stops 24 (see FIG. 6). The slots 90 in the stopper positioner 84 rotationally connect the stopper 66 to the positioner 84, while rotation of the end cap 82 rotates the retainer stop 80 to release the stopper 66 while needle seat stops 92 rotate the needle seat 40 to release the needle seat and thus the needle 26 from the cylinder 10. FIG. 6 more clearly depicts one of the elongate guides 106 separated axially by gap 105 from tube lock 104. Retaining flange 103 on tube 62 (see FIG. 4) fits within the gap 105 to axially secure the tube to the cylinder 10.

Various techniques have been devised for selectively connecting a plunger to a needle seat to withdraw the needle seat to a retracted position with the plunger. A feature of the invention is to combine selected features of the stopper 66 to maintain a vacuum within the tube 62, while the axial length of the stopper is penetrated by the posterior end 30 of the needle 26 to axially connect the stopper 66 to the needle 26. Penetration of the needle into the elastomeric material of the stopper 66 thus connects the stopper to the needle. In most applications, the posterior end of the needle may be positioned within the stopper 66 to seal off the passageway in the needle. Alternatively, the posterior end of the needle could pass through the stopper yet be reliably sealed with and carried with the stopper as it moves to the needle retracted position due to frictional engagement, since the force retaining the needle seat and the stopper in their initial position has been eliminated when the tube 62 is rotated relative to the cylinder 10.

When the health care worker rotates the tube 62 using sheath 64, the plurality of circumferentially spaced slots 76 in the retainer 70 become aligned with the circumferentially spaced tabs 68 to release the stopper 66 to the needle retracted position. The slot 78 in the stopper retainer 70 forms a cap stop which engages the retainer stop 80 on the cap 82 to rotationally connect the cap 82 to the retainer 70. During this brief rotation, the tube 62 rotates relative to the stopper 66, which is held stationary by the stopper positioner 84 rotationally connected to the cylinder 10 by stopper positioner stops 24. Stopper positioner 84 thus provides engagement with both stopper tab 68 and the stopper tab stop 24 on the cylinder 10 to rotationally connect the stopper 66 to the cylinder 10.

So that forces may be equally distributed and thereby minimize misalignment problems between the movable components, preferably a plurality of circumferentially spaced stopper tabs 68 are provided on the stopper, and similarly spaced tabs and slots on the stopper retainer 70 connect and release the stopper 66, as described above. The stopper positioner 84 provides a plurality of circumferentially spaced and axially extending tabs 88 to rotationally lock the stopper positioner 84 with the cylinder 10. A plurality of circumferentially spaced slots rotationally lock the stopper positioner 84 with similarly spaced tabs 68 on the stopper 66. The needle seat 40 includes a plurality of circumferentially spaced cap stops 52 for engagement with the stops 92 on the end cap 82. By providing a plurality of circumferentially spaced tabs and slots in the interacting components as shown in FIGS. 1 and 2, and also by utilizing relatively few components which can be easily and economically manufactured, the stopper 66 is released by the one quarter rotation of the tube 62 relative to the cylinder 10, thereby reliably withdrawing the anterior end 28 of the needle into the tube 62 and thus also into the cylinder 10 as shown in FIG. 5. The released needle 26 thus passes through each of the annular end cap 82, the annular stopper positioner 84, and the annular stopper retainer 70. Alternative embodiments could cause release upon one-third turn or one-half turn, although no more than one-half turn of the tube 62 preferably is required to release the needle seat and the stopper.

A stopper positioner for performing the function of positioner 84 as described above is preferably desired to rotationally fix the stopper tabs, such as tabs 68, to the hollow cylinder 10. In other embodiments, a stopper positioner may be eliminated and the stopper tabs 68 rotationally secured to the cylinder without an intervening component. Preferably a stopper retainer, such as retainer 70, the stopper positioner, such as positioner 84, and the end cap 82 are each annular components with respective tabs and/or slots as discussed herein positioned circumferentially about the component for high reliability with a relatively low manufacturing cost. In other embodiments, these members may not have an annular configuration. The members could, for example, have a c-shaped configuration or could be otherwise configured.

The blood sampling assembly of the present invention may be economically manufactured while at the same time providing a very high degree of protection to the health care worker. By relying upon a vacuum, the operator need not generate the force which will retract the needle into the receiving member. Also, by arranging the tabs and slots as discussed herein, a simple one quarter turn of the tube 62 by the health care worker will release the needle 26 from the cylinder 10 and also release the stopper 66 so that vacuum draws the needle into the tube 62. The device may also be designed with a relatively high degree of safety. As shown in FIG. 5, the stopper 66 is moved to its fartherest end within tube 62. Even if the stopper were spaced substantially from the end of the closed end of the tube 62, the needle 26 will still be within the tube 62.

The blood sampling assembly of the present invention allows blood to be obtained in a conventional manner, wherein the hollow cylinder is sized to receive one or more vials when pressed into the posterior end of the needle. After the desired number of blood samples have been obtained, the health care worker inserts snaps in, and rotates the tube 62 relative to cylinder 10, and the needle is automatically withdrawn into the tube 62. The assembly as shown in FIG. 5 may then be discarded. In the unlikely event that the needle should not be retracted, the health care worker, upon rotating the tube 62 one quarter turn, can observe that the needle has not been retracted and may therefore follow established safety procedures.

It will be understood by those skilled in the art that the embodiment shown and described is exemplary and various other modifications may be made in the practice of the invention. Accordingly, the scope of the invention should be understood to include such modifications which are within the spirit of the invention.

What is claimed is:

1. A blood sampling assembly with a retractable needle for use to obtain a blood sample within a vial, such that an end of the needle is adapted to be inserted into a patient and an opposed end of the needle is sealed with the vial to obtain the blood sample, the blood sampling assembly comprising:

a hollow cylinder having a needle end and an opposed extractor end, the cylinder including circumferentially spaced needle seat tabs and needle seat slots each between spaced needle seat tabs, the cylinder further including a stopper tab stop;

a needle seat for supporting the needle on the cylinder, the needle seat including circumferentially spaced cylinder tabs each in engagement with a respective needle seat tab to temporarily fix the needle seat to the cylinder, the needle seat including cylinder slots each between spaced cylinder tabs and circumferentially aligned with a respective needle seat tab to release the needle seat and the needle from the cylinder, the needle seat further including a cap stop; and an extractor assembly for positioning at least partially within the extractor end of the cylinder, the extractor assembly including a closed end tube containing a vacuum, a stopper in sealed engagement with an interior surface of the tube and axially movable between an initial position and a needle retracted position, the stopper receiving therein the opposed end of the needle, a stopper tab axially secured to the stopper, the stopper tab stop on the cylinder preventing rotation of the stopper tab with the tube, a stopper retainer rotatable with the tube between a retaining position for temporarily fixing the stopper in the initial position and a release position for releasing the stopper to move to the needle retracted position, the stopper retainer including a retainer tab in engagement with the stopper tab when the stopper retainer is in the retaining position and a slot in circumferential alignment with the stopper tab when the stopper retainer is in the release position, and an end cap rotatable with the tube and including a needle seat stop for engagement with the cap stop, such that rotation of the tube rotates the end cap, the stopper retainer, and the needle seat relative to the cylinder to release the needle seat and the stopper and the stopper is moved to the needle retracted position by the vacuum within the tube.

2. The blood sampling assembly as defined in claim 1, wherein the stopper retainer includes a cap stop and the cap includes a retainer stop, such that engagement of the cap stop and the retainer stop prevents rotation of the stopper retainer relative to the cap.

3. The blood sampling assembly as defined in claim 1, further comprising:

a plurality of circumferentially spaced stopper tabs each axially secured to the stopper; and the stopper retainer includes a corresponding plurality of retainer tabs circumferentially spaced each in engagement with a respective stopper tab when the stopper retainer is in the retaining position, the stopper retainer further including a corresponding plurality of circumferentially spaced slots each in circumferential alignment with a respective stopper tab when the stopper retainer is in the release position.

4. The blood sampling assembly as defined in claim 1, wherein the stopper tab is rotationally secured to the stopper, such that the tube rotates relative to the stopper when the tube is rotated relative to the cylinder.

5. The blood sampling assembly as defined in claim 1, wherein the stopper retainer is an annular member which includes a throughbore for passing the needle seat through the stopper retainer when the stopper is moved to the needle retracted position.

6. The blood sampling assembly as defined in claim 1, wherein the end cap is an annular member which includes a throughbore for passing the needle seat through the end cap when the stopper is moved to the needle retracted position.

7. The blood sampling assembly as defined in claim 1, further comprising:

a stopper positioner in engagement with both the stopper tab stop and the stopper tab for preventing rotation of the stopper tab during rotation of the tube.

8. The blood sampling assembly as defined in claim 7, further comprising:

a plurality of stopper tabs each axially secured to the stopper;

the cylinder having a plurality of circumferentially spaced stopper tab stops; and the stopper positioner having a plurality of axially extending cylinder stops each in engagement with a respective stopper tab stop, the stopper positioner including a plurality of circumferentially spaced slots each in circumferential alignment with a corresponding stopper tab for rotatably securing the plurality of stopper tabs to the cylinder.

9. The blood sampling assembly as defined in claim 7, wherein the stopper positioner is an annular member which includes a throughbore for passing the needle seat through the stopper positioner when the stopper is moved to the needle retracted position.

10. The blood sampling assembly as defined in claim 1, further comprising:

the needle seat including a plurality of circumferentially spaced cap stops and the cap including a plurality of circumferentially spaced needle seat stops, such that each needle seat stop engages a corresponding cap stop to rotate the needle seat during release of the needle seat from the cylinder; and the needle seat including a needle seat tab stop for limiting rotation of the needle seat with respect to the cylinder when the cylinder slots on the needle seat are circumferentially aligned with the needle seat tabs on the cylinder.

11. A method of retracting a needle from a cylinder, the needle having an end for insertion into a patient such that a vial is pressed over an opposed end of the needle to obtain a blood sample, the method comprising:

providing a cylinder having a needle end and an opposed extractor end;

providing circumferentially spaced needle seat tabs and needle seat slots each between spaced needle seat tabs on the cylinder;

providing a stopper tab stop on the cylinder;

engaging circumferentially spaced cylinder tabs on a needle seat each with a respective needle seat tab to support the needle seat on the cylinder;

providing cylinder slots each between the spaced cylinder tabs on the needle seat;

providing a cap stop on the needle seat;

providing a closed end tube containing a vacuum and a stopper in sealed engagement with the tube and axially movable between an initial position and a needle retracted position;

axially securing a stopper tab to the stopper;

engaging a retainer tab on a stopper retainer with the stopper tab when the stopper tab is in a retaining position;

providing an end cap rotatable with the tube, the end cap including a needle seat stop;

inserting the tube at least partially within the extractor end of the cylinder such that the opposed end of the needle is within the stopper;

engaging the stopper tab stop on the cylinder with the stopper tab to prevent rotation of the stopper tab; and rotating the tube, the end cap and the stopper retainer from a retaining position for retaining the stopper in the initial position to a release position for releasing the stopper to move to the retracted position, such that a slot in the stopper retainer is circumferentially aligned with the stopper tab when the stopper retainer is in the release position and the cylinder slots on the needle seat are each circumferentially aligned with a respective needle seat tab on the cylinder to release the needle seat and the stopper so that the stopper may move to the needle retracted position within the tube by the vacuum.

12. The method as defined in claim 11, further comprising:

engaging the stopper retainer and the cap to prevent rotation of the stopper retainer relative to the cap; and engaging a stopper tab positioner with both the stopper tab stop on the cylinder and the stopper tab for preventing rotation of the stopper tab during rotation of the tube.

13. The method as defined in claim 11, further comprising:

the stopper having an axial length sealing surface in sealing engagement with the tube; and positioning the stopper within one axial sealing length from an end of the tube, such that the vacuum within substantially the entire length of the tube withdraws the stopper to the needle retracted position.

14. A blood sampling assembly with a retractable needle for use to obtain a blood sample within a vial, such that an end of the needle is adapted to be inserted into a patient and an opposed end of the needle is sealed with the vial to obtain the blood sample, the blood sampling assembly comprising:

a hollow cylinder having a needle end and an opposed extractor end, the cylinder including circumferentially spaced needle seat tabs and needle seat slots each between spaced needle seat tabs, the cylinder further including a stopper tab stop;

a needle seat for supporting the needle on the cylinder, the needle seat including circumferentially spaced cylinder tabs each in engagement with a respective needle seat tab to temporarily fix the needle seat to the cylinder, the needle seat including cylinder slots each between spaced cylinder tabs and circumferentially aligned with a respective needle seat tab to release the needle seat and the needle from the cylinder, the needle seat further including a cap stop; and an extractor assembly for positioning at least partially within the extractor end of the cylinder, the extractor assembly including a closed end tube containing a vacuum, a stopper in sealed engagement with an interior surface of the tube and axially movable between an initial position and a needle retracted position, the stopper receiving therein the opposed end of the needle, a stopper tab axially secured to the stopper, a stopper positioner in engagement with both the stopper tab stop on the cylinder and the stopper tab for preventing rotation of the stopper tab during rotation of the tube, an annular stopper retainer including a throughbore and rotatable with the tube between a retaining position for temporarily fixing the stopper in the initial position and a release position for releasing the stopper to move to the needle retracted position, a retainer tab on the annular stopper retainer in engagement with the stopper tab when the stopper retainer is in the retaining position and a slot in circumferential alignment with the stopper tab when the stopper retainer is in the release position, and an annular end cap rotatable with the tube and including a throughbore and a needle seat stop for engagement with the cap stop, such that rotation of the tube rotates the end cap, the stopper retainer, and the needle seat relative to the cylinder to release the needle seat and the stopper and the stopper is moved to the needle retracted position by the vacuum within the tube.

15. The blood sampling assembly as defined in claim 14, further comprising:

a plurality of stopper tabs each axially secured to the stopper;

the cylinder having a plurality of circumferentially spaced stopper tab stops; and the stopper positioner having a plurality of axially extending cylinder stops each in engagement with a respective stopper tab stop, the stop positioner including a plurality of circumferentially spaced slots each in circumferential alignment with a corresponding stopper tab for rotatably securing the plurality of stopper tabs to the cylinder.

16. The blood sampling assembly as defined in claim 14, further comprising:

the needle seat including a plurality of circumferentially spaced cap stops and the cap including a plurality of circumferentially spaced needle seat stops, such that each needle seat stop engages a corresponding cap stop to rotate the needle seat during release of the needle seat from the cylinder; and the needle seat including a needle seat tab stop for limiting rotation of the needle seat with respect to the cylinder when the cylinder slots on the needle seat are circumferentially aligned with the needle seat tabs on the cylinder.

17. The blood sampling assembly as defined in claim 14, wherein the stopper has an axial length sealing surface in sealing engagement with the tube, and a final sealing surface on the stopper is positioned within one axial sealing length from an end of the tube, such that the vacuum within substantially the entire length of the tube withdraws the stopper to the needle retracted position.

18. The blood sampling assembly as defined in claim 14, wherein the stopper retainer includes a cap stop and the cap includes a retainer stop, such that engagement of the cap stop and the retainer stop prevents rotation of the stopper retainer relative to the cap.

19. The blood sampling assembly as defined in claim 14, further comprising:

a plurality of circumferentially spaced stopper tabs each axially secured to the stopper; and the stopper retainer includes a corresponding plurality of retainer tabs circumferentially spaced each in engagement with a respective stopper tab when the stopper retainer is in the retaining position, the stopper retainer further including a corresponding plurality of circumferentially spaced slots each in circumferential alignment with a respective stopper tab when the stopper retainer is in the release position.

20. The blood sampling assembly as defined in claim 14, further comprising:

the needle seat including a needle seat tab stop for limiting rotation of the needle seat with respect to the cylinder when the cylinder slots on the needle seat are circumferentially aligned with the needle seat tabs on the cylinder.

* * * * *